United States Patent [19]

Heller et al.

[11] Patent Number: 5,373,727

[45] Date of Patent: Dec. 20, 1994

[54] MINIPOROPERMEAMETER

[75] Inventors: John P. Heller; James V. McLemore, both of Socorro, N. Mex.; Zhongming Chen, Bryan, Tex.

[73] Assignee: New Mexico Tech Research Foundation, Socorro, N. Mex.

[21] Appl. No.: 48,712

[22] Filed: Apr. 16, 1993

[51] Int. Cl.⁵ .......................................... G01N 15/00
[52] U.S. Cl. .......................................................... 73/38
[58] Field of Search ............................................. 73/38

[56] References Cited

U.S. PATENT DOCUMENTS

| | | | |
|---|---|---|---|
| 2,913,897 | 11/1959 | Kirkham et al. | 73/38 |
| 2,949,766 | 8/1960 | Kirkham et al. | 73/38 |
| 3,241,357 | 3/1966 | Kellner et al. | 73/38 |
| 3,839,899 | 10/1974 | McMillen | 73/38 |
| 4,052,885 | 10/1977 | Shuck | 73/38 |
| 4,555,934 | 12/1985 | Freeman et al. | 73/38 |
| 4,573,342 | 3/1986 | Jones | 73/38 |
| 4,627,270 | 12/1986 | Jones | 73/38 |
| 4,649,737 | 3/1987 | Jones | 73/38 |
| 4,864,845 | 9/1989 | Chandler et al. | 73/38 |
| 4,961,343 | 10/1990 | Boone | 73/152 |
| 5,159,828 | 11/1992 | Steiger et al. | 73/38 |
| 5,261,267 | 11/1993 | Kamath et al. | 73/38 |

FOREIGN PATENT DOCUMENTS 909627 2/1982 U.S.S.R. ................................. 73/38

OTHER PUBLICATIONS

"Mathematical Basis for Permeability and Porosity Measurements by Minipermeameter," by Zhongming Chen, Thesis, Petroleum Engineering Department, New Mexico Institute of Mining and Technology, entire thesis, 200 pages (Apr. 1992)(not yet publicly disclosed).

"The Prediction of Oil Recovery by Water Flood," by Herman Dykstra et al., Secondary Recovery of Oil in the United States, American Petroleum Institute, Chapter 12, pp. 160-174 (1950).

"Geologically-Sensible Modeling of the Spatial Distribution of Permeability in Eolian Deposits: Page Sandstone (Jurassic), Northern Arizona," by David J. Goggin, Dissertation, Petroleum Engineering Department, University of Texas at Austin, Chapter V, Field Measurement of Permeability, pp. 222-272 (1988).

"A Theoretical and Experimental Analysis of Minipermeameter Response Including Gas Slippage and High Velocity Flow Effects," by David J. Goggin et al., In Situ, vol. 12, Nos. 1 and 2, pp. 79-116 (1988).

"The PRRC Automatic Scanning Minipermeameter," by J. P. Heller, PRRC No. 92-20, pp. 1-14 (Jun. 1992).

(List continued on next page.)

Primary Examiner—Hezron E. Williams
Assistant Examiner—Joseph W. Roskos
Attorney, Agent, or Firm—Rod D. Baker; Deborah A. Peacock

[57] ABSTRACT

The disclosure relates to an apparatus and method for determining the permeability and the porosity of small sections at and just below the surface of a slabbed sample of porous rock or other material. The measurement is performed by forcing air or other gas through a central passageway of a deformable (e.g. rubber) probe tip pressed against the surface of the sample to be tested. Permeability of the matter directly under the probe tip is computed from the ratio of flow rate into the sample to the pressure drop between the gas in the probe-tip and the ambient atmosphere. A preferred and an alternative means for measuring flow rate are disclosed involving the use of an optical interferometer to detect displacement of a bellows chamber. The apparatus of the invention includes a fact-acting valve such that immediately after calculation of the permeability of the sample under defined conditions, a precise value of the porosity of the same sample may be computed from the transient pressure change that is observed after cutting off air flow into the sample from the probe.

41 Claims, 8 Drawing Sheets

OTHER PUBLICATIONS

"The Profile Permeameter: A New, Fast, Accurate Minipermeameter," by S. C. Jones, Society of Petroleum Engineers, SPE 24757, 67th Annual Technical Conf. and Exhibition of the SPE, Washington, D.C., pp. 973–983 (Oct. 4–7, 1992).

"Etude des Heterogeneites de Permeabilites dans Les Milieux Poreux," (Study of Heterogeneities in a Natural Porous Medium), by Y. Morineau et al., partial English translation cover page, Compte rendu du IIeme Colloque ARTFP, Rueil-Malmaison, France, pp. 18 and 274–299 (Jun. 3, 1965).

"High Resolution Probe Permeability: An Aid to Reservoir Description," by Graham M. Robertson et al. *Advances in Core Evaluation Accuracy and Precision in Reserves Estimation*, Paul F. Worthington (ed.), Gordon and Breach Science Publishers, Reviewed Proceedings of the 1st Soc. of Core Analysis European Core Analysis Symposium, London, UK, pp. 495–520 (May 21–23, 1990).

MINIPOROPERMEAMETER

BACKGROUND OF THE INVENTION

1. Field of the Invention (Technical Field)

This invention relates to means and methods for determining the porosity and permeability of materials, especially rocks and minerals.

2. Background Art

There are a variety of existing devices for measuring the porosity or permeability of solid substances. Knowledge of a particular material's porosity or permeability may be valuable in a variety of academic and industrial endeavors. A principal field where devices measuring porosity and/or permeability find ready utility is the oil and gas extraction industry. The porosity and permeability of a natural gas or petroleum bearing rock formation have direct and substantial implications for the economical development of the formation. Porosity, which is the fraction of the rock's bulk volume that consists of interconnected porespace, is essential in the evaluation of fluid content of subsurface formations. Information regarding permeability, which is a measure of the rate at which fluid flows through the rock under an applied pressure gradient, is similarly vital for the analysis or design of processes involving subsurface flow.

Consequently, many efforts have been made to provide a device or method for determining these critical material properties of geological formations. Laboratory measurement of these properties usually has been performed by retrieving sample or "cores" from wellbores drilled into the formation. After cleaning, which may involve using hydrocarbon solvents to remove remaining crude oil, the porosity of the dry core is typically determined using a gas expansion technique. Air flow in different directions through the core is commonly measured by enclosing the core in a rubber sleeve equipped with input and output flow ports. Generally, the flow of the test fluid is confined within known boundaries; except for the constant pressure boundaries at which fluid is injected or recovered, the no-flow boundaries are established as such by the elastomeric boot or sleeve pressed against the rock (or occasionally by a plastic coating). From the pressure drop across the core and from flow rate during steady-state flow, the permeability of the sample is then computed by use of equations derived from Darcy's Law.

The non-destructive measurement of permeability on selected small regions of larger samples of rock can be accomplished by use of a flexible-tipped instrument known in the art as the "minipermeameter" or "micropermeameter". The method involved was first described by H. Dykstra and R. L. Parsons under the latter name in "*The Prediction of Oil Recovery by Waterflood,*" *Secondary Recovery of Oil in the United States*, Chap. 12, pp. 160–174 (American Petroleum Institute, New York, 1950) (presented as Paper #801-24k at the Spring Meeting of the Pacific Coast District, Division of Production, American Petroleum Institute, Biltmore Hotel Los Angeles May 6–7, 1948). Dykstra and Parsons used the perpendicularly-cut end of a soft rubber tube as their probe-tip. These authors investigated the distribution of permeability at the end-face of a core plug, finding significant variability even on this relatively small area.

A somewhat later manifestation of the instrument is described by Morineau, Simandoux and Dupuy in "Etude des heterogeneities de permeabilites dans les milieux poreux," Compte rendu du IIeme Colloque ARTFP, pp. 273–299 (Rueil, May 31–Jun 4, 1965). These investigators showed that there is a significant effect of core heterogeneity on recovery efficiency—this time in solvent displacement experiments.

A major step forward in the rational use of the minipermeameter was taken by David Goggin in his Ph.D. thesis, "Geologically-Sensible Modelling of the Spatial Distribution of Permeability in Eolian Deposits: Page Sandstone (Jurassic), Northern Arizona," Petroleum Engineering Department, University of Texas at Austin, Chapter V, Field Measurement of Permeability, pp. 222–272 (1988), and in an article by Goggin, Thrasher and Lake entitled "A Theoretical and Experimental Analysis of Minipermeameter Response including Gas Slippage and High Velocity Flow Effects," In Situ 12, Nos. 1 & 2, pp 79–116 (1988). In these works, Goggin, et. al. give an analytic treatment of the flow below the probe-tip, complete with numerical simulation to compute the appropriate multiplier by which the permeability can be computed from the flow rate, the pressure in the probe, the dimensions of the probe and the atmospheric pressure and viscosity of air.

Although in principle the minipermeameter is best used on a slabbed surface of infinite extent, the thickness of the slab and the proximity to the probe of other boundaries has obvious effects because the injected air may thus gain alternate pathways to the atmosphere through the extraneous boundaries at the sides or lower side of the slab. Goggin and his collaborators evaluated the influence of both slab thickness and of (cylindrically symmetric) side boundaries, by use of the numerical simulator. As a result of these calculations, it is evident that air flow out of the extraneous boundaries has negligible effect on the measured permeability, so long as these boundaries are further from the probe than about five times the diameter of the tip.

Since Goggin's work, there have been several other versions of the minipermeameter described in the literature. These have included works by Robertson and McPhee in "High Resolution Probe Permeability: An Aid to Reservoir Description," *Advances in Core Evaluation Accuracy and Precision in Reserves Estimation*, Reviewed Proceedings of the First Society of Core Analysis European Core Analysis Symposium, (London, UK, May 21–23, 1990, Paul F. Worthington (ed.), Gordon and Breach Science Publishers (1990)); and by S. Jones in "The Profile Permeameter: A New, Fast, Accurate Minipermeameter," SPE 24757, pre-print of paper presented at the 67th Annual Technical Conference of the SPE, Washington D.C. (1992). The major motivation for the work cited has been to facilitate the study of local rock heterogeneities. As such, some of the devices reported have been adapted to portable use by geologists for the examination of rock outcrops, and some have been predominately laboratory instruments adapted to make closely-spaced measurements at accurately known positions on the face of slabbed cores or larger rock samples. The general design has also been adapted into commercial instruments.

Supplementing Goggin's numerical work has been that of Zhongming Chen in "Mathematical Basis for Permeability and Porosity Measurements by Minipermeameter," Petroleum Engineering Department, New Mexico Institute of Mining and Technology, Socorro, New Mexico (April, 1992), the teachings of which are incorporated herein by reference, which not only extends the steady-state flow computations, but also computes the transient pressure change inside the rock and at the probe-tip during the brief interval of time after cut-off of the air flow into the entry area defined by the tip. The results of these computations make possible the computation of porosity in a manner described in succeeding paragraphs hereafter.

J. P. Heller has also published a detailed description of a working permeameter which applies many of the principles and features herein disclosed to perform rapid and accurate measurements of samples permeability. J.P. Heller, "The PRRC Automatic Scanning Minipermeameter," PRRC No. 92-20 (June, 1990), available from the New Mexico Petroleum Recovery Research Center, New Mexico Institute of Mining and Technology, Socorro, N. Mex., the teachings of which are expressly incorporated herein by reference.

In addition to the academic research reflected in the foregoing references, a number of apparatuses in the field are the subjects of issued patents.

U.S. Pat. No. 4,961,343 entitled, *Method for Determining Permeability in Hydrocarbon Wells*, to Boone discloses a method of determining the permeability of subsurface geological formations by monitoring the character and content of the drilling mud coming to the surface during oil and gas drilling operations.

U.S. Pat. No. 4,864,845 entitled *Electronic Field Permeameter*, to Chandler, et al., discloses an electronic field permeameter utilizing mass flow controllers to regulate and measure the flow of gas to the sample and pressure transducers to measure the pressure of the gas applied to the sample. The flow rate and pressure are electronically monitored and processed using microcomputer technology mathematically to calculate permeability. Constant pressure is maintained using a conventional pressure regulator.

U.S. Pat. Nos. 4,649,737 entitled *Apparatus and Method for Automatic Testing of Core Samples*, and 4,573,342 entitled *Apparatus and Method for the Automatic Porosity and Permeability Testing of Multiple Core Samples*, to Jones describes a carousel apparatus for testing in seriatim a plurality of core samples. The apparatus is directed primarily toward the automated, mechanized, movement and loading of a large number of samples, and is usable with a variety of instruments for testing permeability or porosity; very few specifics concerning actual permeameter or porometer structure or function are disclosed.

U.S. Pat. No. 4,555,934 entitled *Method and Apparatus for Nonsteady State Testing of Permeability* to Freeman, et al., teaches an apparatus and method for measuring the permeability of a substance during a non-steady state flow of fluid through a core sample. A change in pressure across the sample is measured over time, and permeability is ascertained as a function of the time-related measure of the pressure change.

U.S. Pat. No. 4,052,885 entitled *Portable Device and Method for Determining Permeability Characteristics of Earth Formations*, to Shuck discloses an apparatus for determining the direction of maximum permeability in surface rock formations. As apparatus serves primarily to perform comparative qualitative analyses of permeability, the precise means of quantifying permeability is not fully disclosed, but is based on flow discharge measurements.

U.S. Pat. No. 3,839,899 entitled *Method and Apparatus for Determining Parameters of Core Samples*, to McMillen teaches an apparatus and method for measuring permeability based on changes in pressure across a core sample over measured time.

U.S.S.R. Patent No. 909627 discloses an apparatus for determining the filtration properties of a soil sample based at least in part upon pressure measurements and application of D'Arcy's Equation.

A need remains, however, for an apparatus capable of measuring both the porosity and the permeability of geological core samples, or other materials, that is easy to use, portable, durable, and reliable.

SUMMARY OF THE INVENTION (DISCLOSURE OF THE INVENTION)

The invention relates to methods and apparatuses for determining the permeability and porosity of materials, especially geological samples and specimens. A basic feature of the invention is that it enables the user to consecutively measure the permeability and the porosity of a sample using a single integrated apparatus. The determination of permeability is made by measuring the rate of a fluid flow through the sample (combined with the application of Darcy's Law and Equations). The measurement of rate of fluid flow is followed immediately by the quantifying the elapsed times required for the pressure of the fluid contained above a sample surface to decrease to two pre-selected levels. By comparing these two elapsed times to corresponding values previously ascertained for substance(s) of known porosity, and applying data acquired in the permeability-measuring phase of the invention, porosity may be determined.

The rate of fluid flow is measured, and constant pressures maintained, through the use of variable volume chamber elements through which the flowing fluid passes. Variable volume chambers may be bellows or diaphragm elements or other modes of enclosing variable volumes of fluid. The variable volume chamber utilizes constant force sources, such as springs or weights, to maintain a constant pressure in the fluid flowing through the sample. Changes in the volume of the variable volume chambers attributable to fluid flow are converted into linear displacements; the invention includes elements (for example, photodetectors or interferometers) for accurately monitoring these linear displacements and converting them to flow rates for use in calculating permeability.

The invention also features a novel valve element wherewith the fluid flow through the sample may be abruptly terminated and a small volume of fluid trapped in an enclosed cavity above the sample surface. A piezometer is provided whereby the decay in fluid pressure within the cavity may be measured and recorded for later comparison with corresponding values of other substances of known porosity, and with calculated permeability, to arrive at porosity value.

It is an object of the present invention to provide a means for measuring both permeability and porosity of a substance in rapid succession and with a single apparatus.

Another object of the present invention is to provide an apparatus for measuring permeability and porosity that is durable and portable.

Still another object of the present invention is to provide a method and apparatus for measuring permeability and porosity that is nondestructive and does not necessarily require the preparation of a core sample.

Still another object of the present invention is to provide a means and method for measuring both permeability and porosity in a relatively short time.

An advantage of the present invention is that the necessary control and computation tasks can be performed automatically by a computer.

Another advantage of the present invention is that it is adaptable for practice either in the field (where the probe is hand-held, and successive measurements made of natural rock formations or construction materials) or in the laboratory (where auxiliary motion control devices can be utilized to make measurements at predetermined spacings on slabbed samples).

In addition to its uses for petroleum geologists for determining both permeability and porosity of oilfield cores, the present invention can be readily practiced to obtain economically important data about many different types of rigid porous media. With the various embodiments of the invention described hereafter, specialized miniporopermeameters can be manufactured for the examination of any of a wide variety of porous materials, including building stone and man-made concrete and ceramics.

Other objects, advantages and novel features and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings:

FIG. 2a is a side view of an alternative embodiment of the variable volume chamber of the present invention with optionally associated film and photodetector elements for detecting motion;

FIG. 2b is a top plan view of the photodetector element of the embodiment of FIG. 2a;

DESCRIPTION OF THE PREFERRED EMBODIMENTS (BEST MODES FOR CARRYING OUT THE INVENTION)

The invention relates to methods and apparatuses for consecutively measuring both porosity and permeability of small portions of material (such as rock) at and just below the position of a probe. In the preferred embodiment of the invention, information regarding the permeability of the sample is measured, immediately followed by the data-gathering required to make a porosity determination of the same portion or sample of rock.

Figure 1:
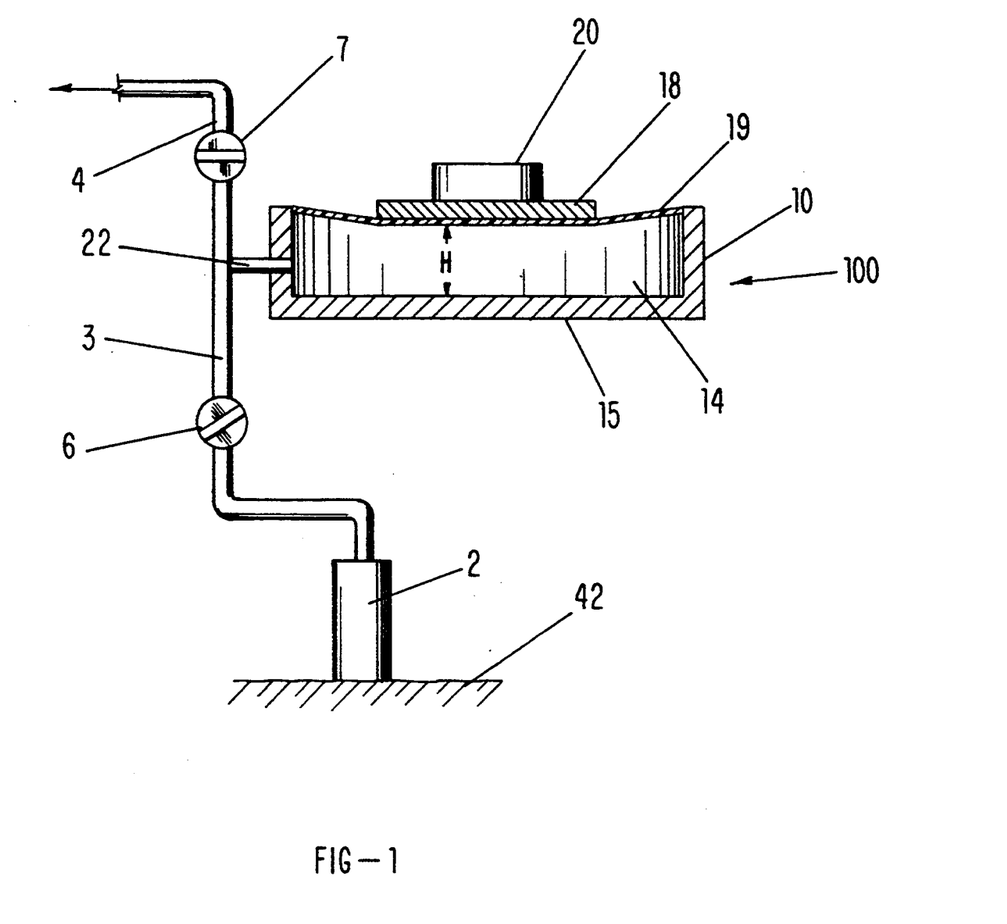
FIG. 1 is a side sectional view of the preferred embodiment of the variable volume chamber of the present invention.
Figure 1A:
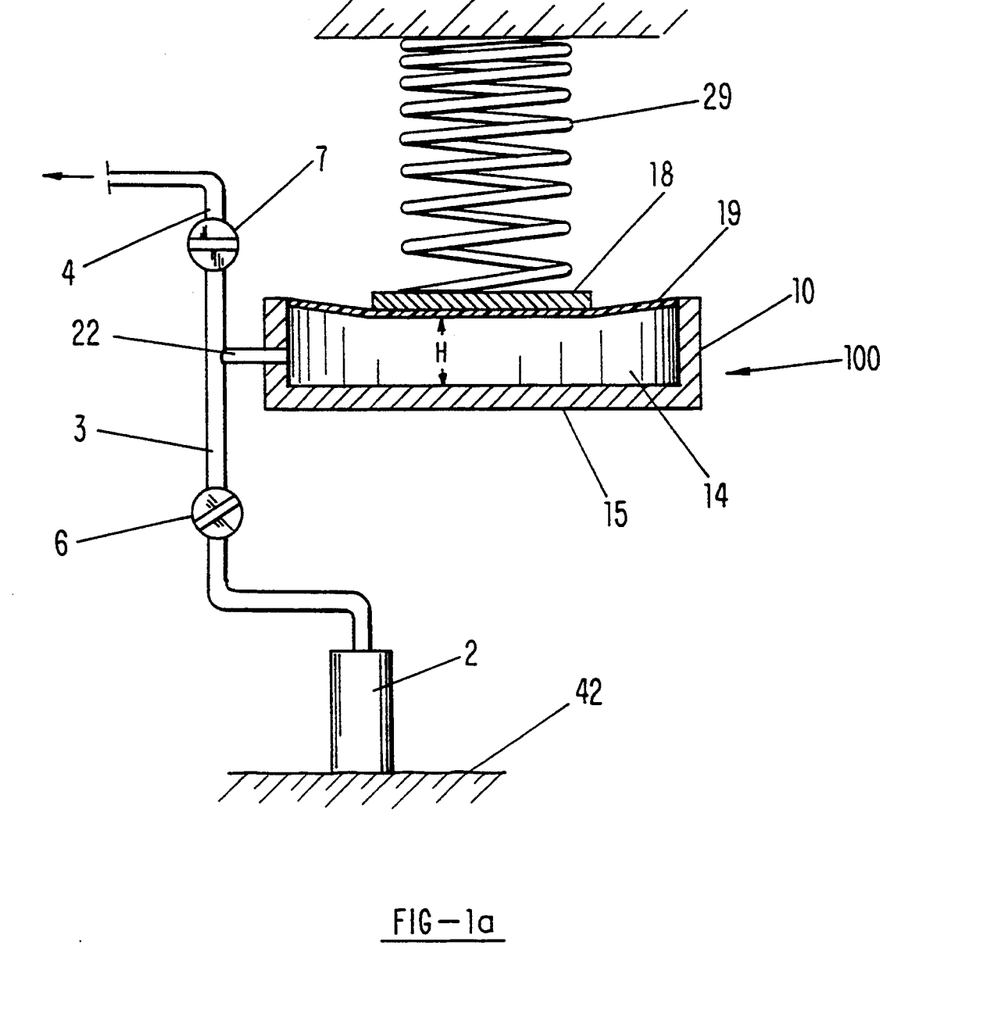
FIG. 1a is a side sectional view of a second embodiment of FIG. 1.
Figures 2A, 2B:
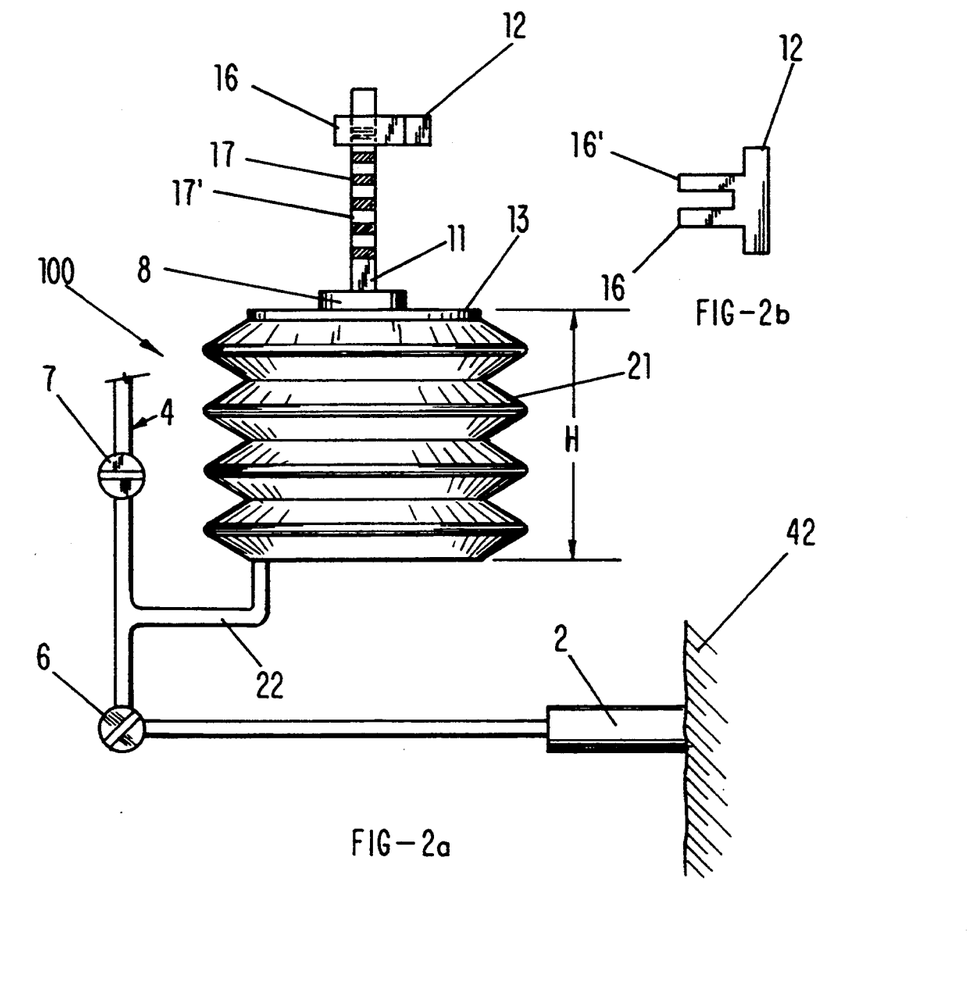
Figure 3:
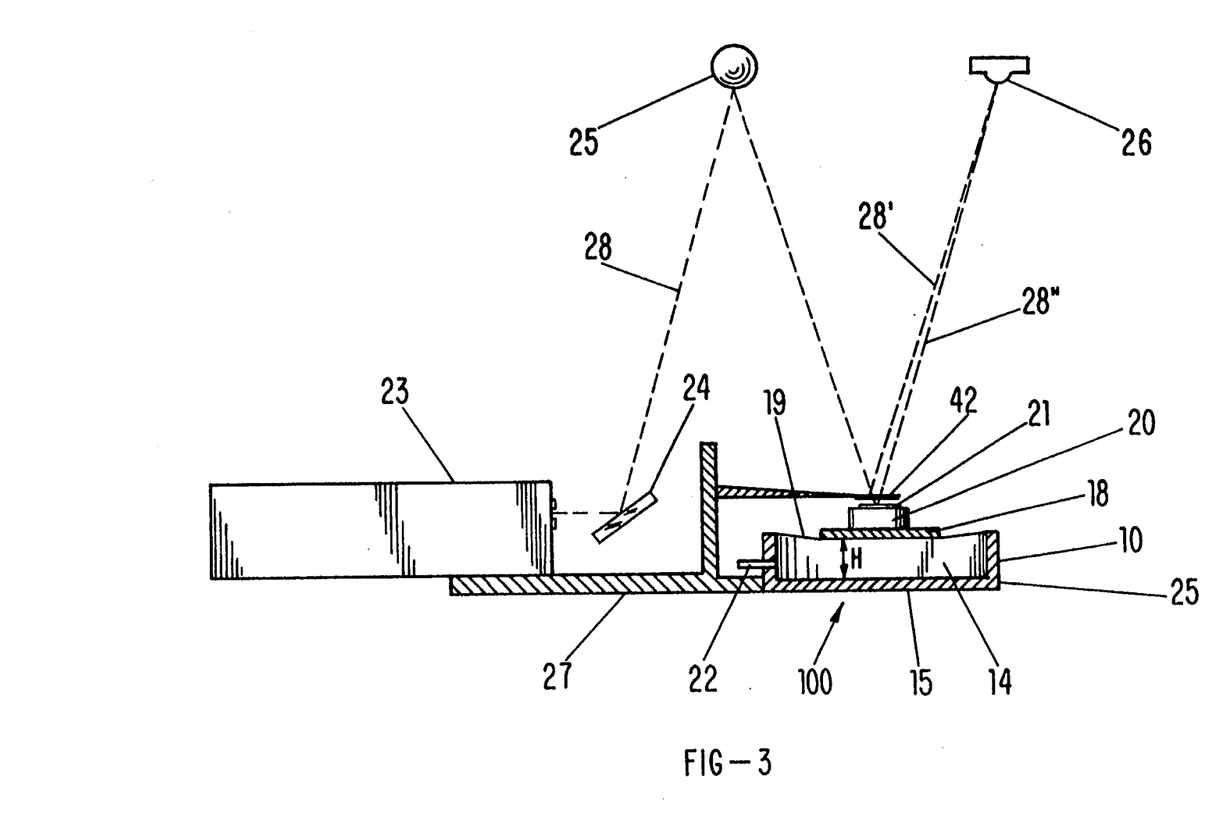
FIG. 3 is a side view of an interferometric system for detecting motion in variable volume chambers, incorporating the FIG. 1 embodiment of the variable volume chamber.

The probe is placed against a surface of the substance to be tested, followed by the practicing of the invention consisting of two general functions performed in succession and preferably under the control of a suitably programmed computer. The first of the processes is directed to the acquisition of data by which substance permeability can be calculated. A novel apparatus and method to obtain this data is described below in detail, and the preferred embodiment is generally illustrated by FIGS. 1-3. Fundamentally, the process of obtaining permeability data consists of measuring the time interval required for a known quantity of air or other fluid, at a known constant pressure, to flow through the probe and then through the sample. From this measured time of discharge, the computer can calculate permeability using known formulae based on Darcy's Equation. After the permeability is calculated from the flow rate, the invention may immediately proceed to the process of gathering data pertaining to sample porosity.

Figure 6:
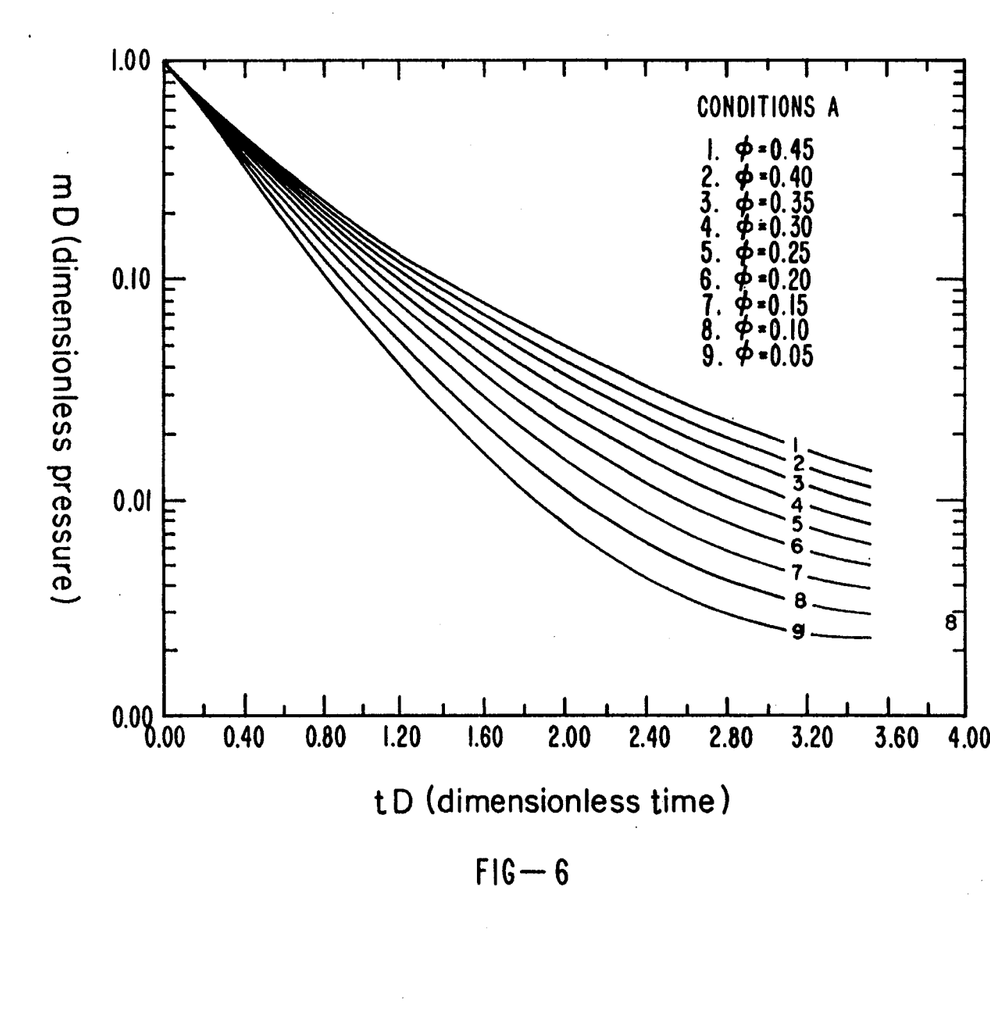
FIG. 6 is a graph of a family of nine pressure decay curves for rock of various given porosities.
Figure 7:
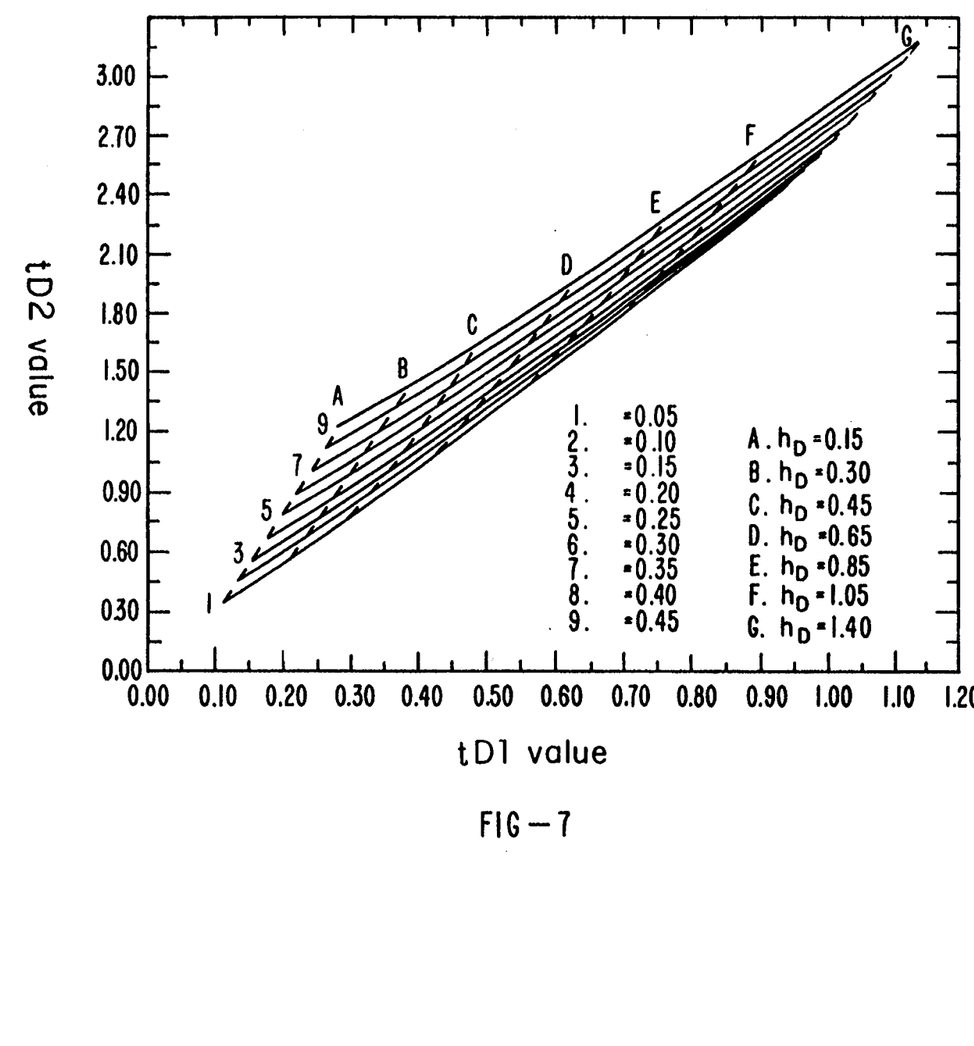
FIG. 7 is a graph of a family of nine calculated curves, for the porosity values of the FIG. 6 embodiment, from which porosity may be determined using known elapsed times for pressure decay to two particular levels.

This second porometric process is commenced with the closing of a novel fast-acting valve mounted within the probe. Also disposed within the probe is a pressure transducer for sensing pressure changes. Illustrations of alternative embodiments of the combined valve-and-probe apparatus are found at FIGS. 4 and 5. Using one of these apparatuses, the flow of fluid into the sample is abruptly stopped, with a minimum amount of fluid trapped in the space or cavity between the sample and the tip of the probe. Having reference to the previously calculated permeability value, the computer can calculate an expected approximate rate at which the cavity pressure will decline, which in turn permits the computer to set the intervals at which pressure measurements will be made to monitor pressure decay. From the measurements then made by the transducer of the changing decay rate, both the sample porosity and the value of the residual cavity volume between probe and sample can be calculated. A typical set of pressure decay curves for different values of rock porosity is shown in FIG. 6, while FIG. 7 illustrates how the decay data can be used to determine the porosity. A suitable computer program determines the porosity from the measurements made to define the pressure decay curve. The calculated values of permeability and porosity may then be displayed and/or stored by the computer.

Thus, according to the invention, permeability is measured by a steady-state flow of air through a probe-tip into the surface of a sample, using the equation developed by Goggin, and porosity is measured by direct observation of the pressure in the tip during the short transient period immediately after terminating the flow through the tip.

Calculation of porosity entails use of the formulae developed by Chen. In this calculation, the value of the permeability of the affected portion of sample must be used, which in turn gives rise to the requirement that permeability must be measured prior to the generation of the transient pressure change for the measurement of porosity. From the measured permeability, it is possible to calculate the upper and lower limits of the decay time that will elapse after shutting off the flow into the sample but before the pressure (at the sample face below the probe) will decline to, say, 5% of its initial value. This information may be conveniently used in the form of a multiplier, by which the measured time can be converted into a dimensionless time. For values of the initial pressure that exceed atmospheric (i.e. for gauge pressures) of only a small fraction of atmospheric pressure, the pressure (expressed as a fraction of the initial gauge pressure) decays along particular curves that are presented in the thesis by Chen, and which depend only on the porosity of the sample and on the relative magnitude of the small cavity existing between the rock face and the diaphragm of the pressure transducer. By a simple computation, these two factors can be separated so that parameters of the measured decay curve can be used to obtain values for both quantities.

The requirement to measure permeability before the porosity does not impose a significant burden either in the complexity of the required control system or in the time needed for measurement of both quantities in rapid succession.

Permeability is determined after measuring the rate of fluid flow through the subject sample and also the pressure differential across the sample. The preferred embodiment of the invention includes improved means for measuring the rate of fluid flow through the subject rock using a variable volume chamber (VVC). A second principal object of the invention, i.e., evaluating porosity, is accomplished by applying the teaching that the pressure transient, observable during the period just after a change in the flow rate into the rock, may be interpreted to give information on material porosity. In the present invention, this flow change preferably is accomplished by completely and suddenly cutting off the flow of gas into the probe. The invention may include either of two embodiments of a fast-acting valve, adapted to this function, that is incorporated into the probe that is held against the sample. The preferred embodiment of the invention incorporates both the fast-acting valve feature that is used to initiate the porosity measurement, and the variable volume chamber that is used for the permeability measurement.

The novel features of the present invention are directed toward overcoming two major problems which would compromise the accuracy of permeability and porosity determinations: the need to accurately measure flow rate during the permeability measurement, and the need to minimize the volume of air within the probe and above the sample in which the transient pressure is evaluated.

The need to accurately time the process of the invention during the permeability measurement is accomplished by detecting the change in contained volume of the variable volume chamber (VVC). FIG. 1 illustrates a preferred embodiment of a VVC suitable for use in the present invention. This form of the VVC consists of a cylindrical rigid vessel 10 enclosing a chamber 14. Vessel 10 is pierced by discharge tube 22 connecting chamber 14 with probe 2 via probe line 3 and also with air pump (not shown) via supply line 4. Disposed on supply line 4 is valve 7, and on probe line 3 is valve 6. Vessel 10 is rigidly closed at its bottom 15. A thin rubber or elastomeric sheet covers and closes the circular opening of the upper end of vessel 10, forming diaphragm 19. Centered on diaphragm 19 is a smaller, rigid circular disk 18 which is forced downward by either a weight 20 or, alternatively, by symmetrically disposed constant-force spring 29 as shown in FIG. 1a. (The use of constant-force springs in lieu of weight 20 presents the advantage of a VVC which functions without regard for its orientation to the earth's gravitational field, i.e., it need not be placed upright upon a level surface; use of weight 20, however, presents advantages of consistency and durability.) The air pressure in the chamber 14 is equal to the ratio of the total gravitational or spring force on disk 18 to the horizontal area of disk 18. The volume of chamber 14 (and thus the quantity of air contained within it) will relate primarily to the height H of the disk 18 above the bottom 15 of vessel 10, and to a lesser extent upon pressure. (The latter, minor, dependence will be a consequence of the pressure dependent curvature of the annular part of diaphragm 19 which is free to deform in response to air pressure differences.)

The height H of disk 18 is measured by any means sufficiently precise so that by timing a decrease in height H the rate of outflow of gas from chamber 14, through discharge tube 22, probe line 3, probe 2, and eventually through sample 42 can be determined within an error of no more than 0.5%. Alternative means for measuring changes in height H are shown in FIGS. 2a, 2b, and 3 and comprise important features of the invention to be described shortly.

To begin the measurement of permeability, the valve 7 is opened and valve 6 is closed. Air, or some other inert fluid, is then pumped into the VVC chamber 14 until the disk 18 has been raised to some standard position. Valve 7 is then closed and valve 6 to probe 2 is opened. Air then flows from chamber 14, out of probe 2 and through the sample 42 to the atmosphere. The timed rate at which this occurs provides data by which the permeability can be calculated.

The rate at which air leaves chamber 14 is expressed by the rate at which diaphragm 19 moves downward. Even if the relationship between the downward velocity of disk 18 and the rate of air flow is nonlinear, a computer program can be written to make the proper allowances. Two different means by which the position of the diaphragm 19 of the VVC may be measured are illustrated in FIGS. 2a, 2b and 3.

If the horizontal cross-sectional area of the VVC is relatively small, a longer vertical stroke can be used without requiring inordinate amount of time to perform the permeability measurement. (While in this disclosure the terms "horizontal" and "vertical" are used as they would conventionally be applied in the figures, it will be understood that the various embodiments of the invention not dependent upon gravity may be practiced in any positional orientation. Only an embodiment of the VVC employing weight 20 is substantially gravity-dependent.) In such a case, the absolute precision requirement in the measurement of height H is not so critical, and the motion can be made with commercially available devices.

FIG. 2a shows the closed top end of a rubber bellows 21 that serves as a VVC having a longer "stroke" and comparatively smaller cross-section, while nevertheless applying many of the concepts and features of the diaphragm/chamber apparatus disclosed above. Top 13 of bellows 21 is forced downward by a centrally placed weight 8 or, alternatively, by symmetrically disposed constant-force springs. Fixed vertically to the bellows 21 is a linear mask, or strip of plastic film 11 (which might be produced photographically) across which are printed alternate, equally-spaced opaque and transparent stripes 17,17'. As air is pumped through supply line 4 and discharge tube 22 into the bellows 21, top 13 rises and the film strip 11 moves upward between the arms 16,16' of a commercial "slot detector" 12 such as the OPTEK model OPB 820S3. Plan view of the slot detector 12 is shown in FIG. 2b. In one arm 16 of the slot detector 12 is a light source (preferably a light-emitting diode, not shown), and in the other arm 16' is a light detector such as a phototransistor (not shown). Accordingly, slot detector 12, when activated by a simple circuit well known in the art, is able to produce a much larger signal when a transparent stripe 17' is between the arms 16,16' of the detector 12, than when an opaque stripe 17 is in the same position. With an appropriate program, a computer that controls the valves 6,7 and monitors the signal from the slot detector 12 is thus able to distinguish and count the stripes 17,17', and time the motion of the movable top 13 of the bellows 21 to which the film strip 11 is attached. The distance and time measurements thus obtained are translated by the computer to evaluate the rate of air flow out of the probe 2 and into the sample 42. As can be appreciated by those skilled in the art, other positive and negative markers can be provided for signalling purposes.

A different situation can arise if the cross-sectional area of the VVC is relatively large. The VVC shown in FIG. 1 illustrates this situation. In this case, only a relatively small motion of the movable diaphragm 19 of the VVC will give a large volumetric change. Smaller distances must therefore be measured to greater absolute precision for timely permeability measurements. An inexpensive means of measuring small distances interferometrically is shown in FIG. 3. Fixed to the movable diaphragm 19 of the VVC 100 is a plane glass reflector 21 which could consist of a microscope cover glass. Above it is placed a second unsilvered glass reflector 42, this one fixed relative to the frame 27 of the apparatus. The distance between the reflectors 21 and 42 thus varies with the position of disk 18 and thus the amount of air in chamber 14. A small, low-power helium neon laser 23 is also fixed to frame 27. The beam 28 from laser 23 is directed upward by diagonal reflector 24 to a ball bearing 25 that reflects beam 28 downward onto the two glass reflectors 21 and 42. Reflected light from them is again directed upwards to photodetector 26. The diagonal reflector 24, the ball bearing 25, and the photodetector 26 are also fixed to the framework 27 of the apparatus (only a portion of frame 27 is shown). Because the light from the laser 23 is nearly monochromatic and coherent over relatively long distances, the pair of light beams 28',28" reflected to detector 26 from plates 21 and 22 interfere with one other. The interference is either constructive (producing a greater response from photodetector 26) or destructive (causing a decrease in the signal), depending on whether the difference in path length between the two reflected beams 28',28" is equal or unequal to a whole number of wavelengths of light. Thus, as the movable diaphragm 19 of the VVC 100 moves up or down, an appropriately programmed computer, to which the photodetector 26 is connected, is again able to count and time the alternations of light and dark in order to determine the rate at which air is being pumped into, or flows out of, chamber 14. Because the wavelength of light from the laser 23 is short ($6.328 \times 10^{-5}$ cm), the interferometric method is capable of measuring very small changes in height H, and can be used to make a volume flow measurement of adequate precision within a relatively short time interval.

It will be readily be observed by a person of ordinary skill in the art that either motion detection apparatus, viz. either the interferometer or the "slot detector," can satisfactorily be adapted for use on either embodiment of the VVC. For example, factors of cost or durability may suggest adapting a "slot detector" photodetector for use upon the diaphragm/rigid chamber embodiment of the VVC.

With the aid of the measurements of rate of outflow from the VVC and known or previously entered constants, a computer is able to calculate the permeability of a hemispherical region of the sample 42 that lies immediately under the probe 2. This calculation is performed in a manner referred to briefly in a previous section, using mathematical formulae developed by Goggin and by Chen in the references cited. Immediately after the permeability measurement, data are then to be collected for the porosity determination, and so it is appropriate to describe at this point the means by which the transient pressure decay is measured.

Two major factors determine the design of the pressure measurement apparatus. The first is that the pressure decay is dependant on both the permeability of the rock below the probe and on the quantity of pressurized air in that region of rock and in the cavity. Generally, this decay must occur quite rapidly, so it is necessary to obtain repetitive pressure measurements quite closely spaced in time. For high permeability rock of low to moderate porosity, the measurement intervals could be as small as ten microseconds. Secondly, in order for the pressure decay measurements to be more responsive to rock porosity than to the pressure cavity volume, the pressure cavity must be small in comparison to the pore volume of the region of rock examined.

Figure 4:
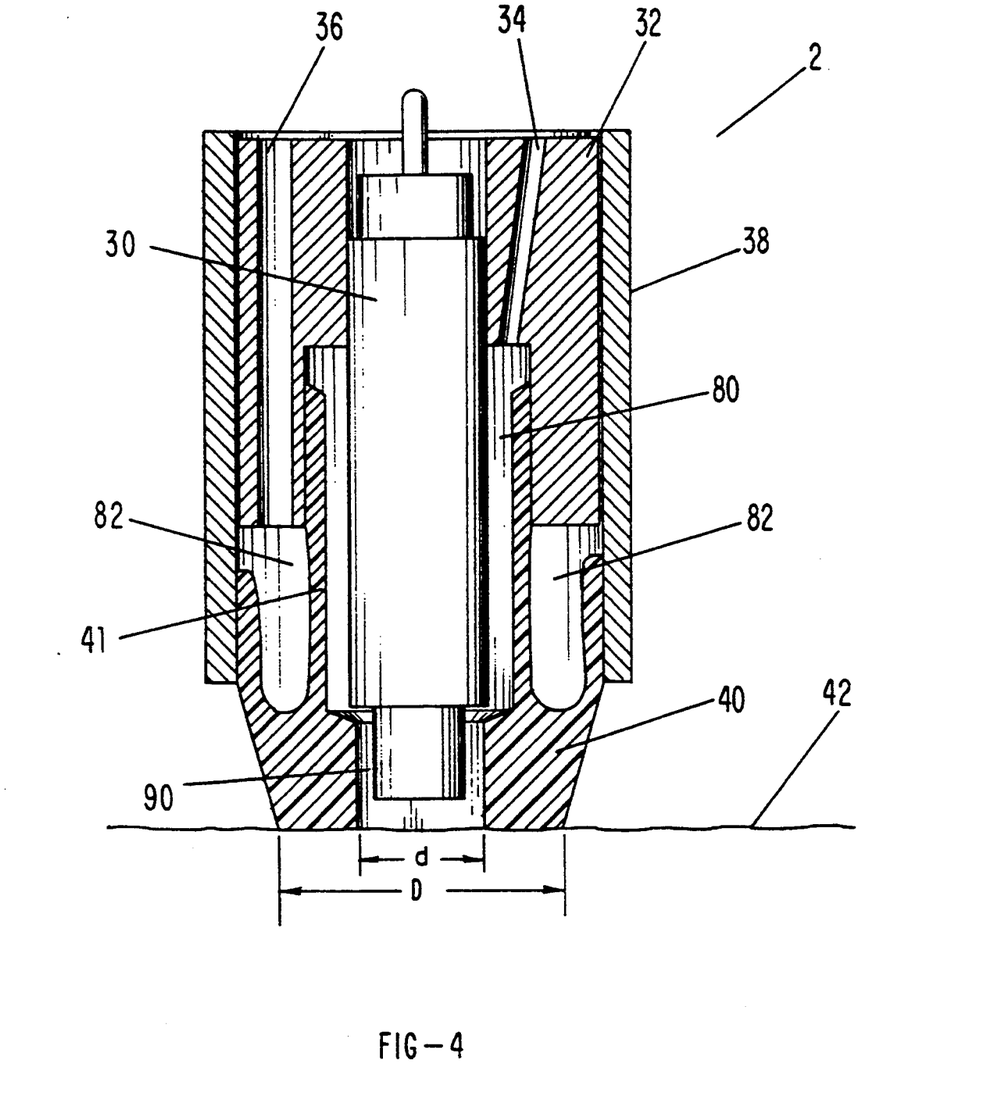
FIG. 4 is a sectional side view of the probe element of the present invention, illustrating the preferred embodiment of the fast-acting shutoff valve system of the present invention.
Figure 5:
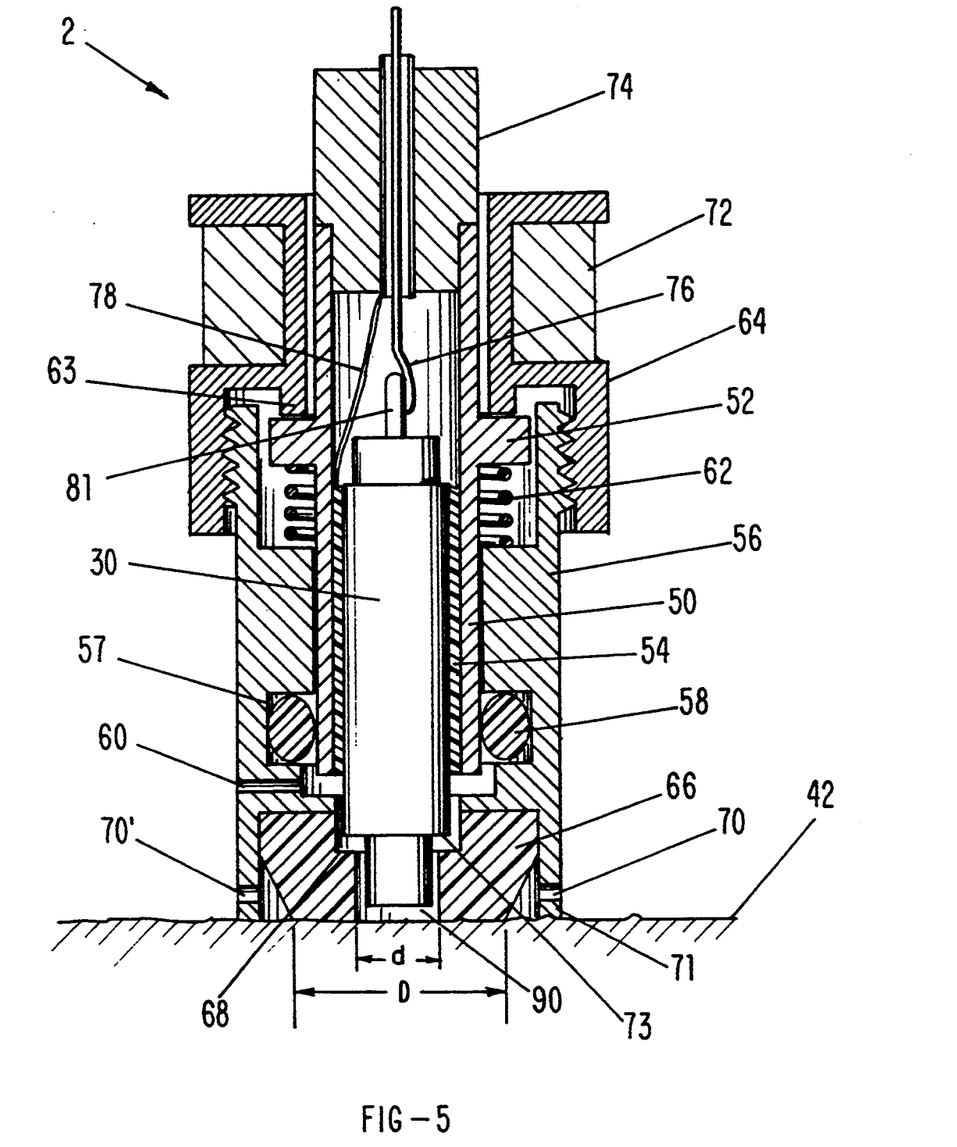
FIG. 5 is an alternative embodiment of the FIG. 4 embodiment.

These two factors are taken into consideration in the design of special probes generally shown at 2 in FIGS. 4 and 5. These probes 2 preferably, but not necessarily, are those used in the embodiments of FIGS. 1, 2a and 2b. The embodiments of FIGS. 1-2b may perform permeability measurements using conventional probes. FIGS. 4 and 5 depict alternative embodiments of the fast-acting valve feature of the invention to be mounted within probe 2. Probe 2 in all embodiments of the invention is connected to a source of pressurized gas (e.g. air, nitrogen) via a flexible tube. Probe 2 is the element of the invention that is placed in direct contact with the rock sample 42 to be tested. In the preferred embodiment, probe 2 and its components are generally cylindrical in shape.

Either of these probes 2 allows the measurement of both permeability (preferably using one of the VVC's disclosed hereinabove) and porosity. Each of probes 2 incorporates a commercially available piezoelectric pressure transducer 30 commonly applied to measure pressure transients resulting from explosions or mechanical shock. This pressure transducer 30 preferably is the Model 105A transducer manufactured by PCB Piezotronics Company of Depew, N.Y. Transducer 30 is small, with a stainless steel diaphragm, and includes a charge amplifier that enables its signal to be gauged by a metering circuit of relatively low input impedance.

Specific attention is directed to FIG. 4, showing the preferred embodiment of probe 2 with transducer 30. Transducer 30 is enclosed within probe 2 and rigidly fastened to brass body 32 of probe 2. The pressure sensitive diaphragm of transducer 30 is at its lower end, and is parallel to the face of rock sample 42 and therefore not shown in FIG. 4. Brass body 32 is penetrated by inner porthole 34, which leads to an inner annular region 80 between transducer 30 and a silicone rubber molding 40. Brass body 32 is also pierced by outer porthole 36, which leads to an outer annular space 82 between the wall 41 of rubber molding 40 and an outer wall 38 attached to brass body 32, preferably by soldering.

With the exception of the inner porthole 34 and the outer porthole 36, the remaining components of the probe apparatus 2 are cylindrically symmetric about the axis of transducer 30. As seen in FIG. 4, the lower end of rubber molding 40 constitutes the tip of the probe 2 and is the portion of the probe 2 which is placed in contact with the rock or other material sample 42. In use, probe 2 is held against the sample 42 with sufficient force so that the lower surface of molding 40 is made to conform to the granular surface of the sample 42, thereby preventing airflow between the two surfaces and constraining the gas in probe 2 to flow down into sample 42, and back out through the portion of sample 42 not covered by the tip 40 of probe 2.

Inner porthole 34 allows gas to flow through it, and through the inner annular space 80 between the transducer 30 and the wall 41 of molding 40, to all the surface of the sample 42 within the inner diameter d of the tip of probe 2 as defined by rubber molding 40. Molding 40 likewise defines the outer diameter D of the area of no-flow boundary imposed by the tip of probe 2.

Outer porthole 36 communicates with the closed outer annular space 82 between the wall 41 of rubber molding 40 and outer wall 38. Except for outer porthole 36, outer annular space 82 is closed; the space 82 can be inflated against transducer 30 by the influence of gas injected thereinto. When fluid, preferably nitrogen gas, is forced through outer porthole 36 into outer annular space 82, rubber wall 41, which is a part of molding 40, is forced against the sides of transducer 30, sealing off cavity 90 (within the inner diameter d of the tip of probe 2 and above the sample 42) from fluid flow through inner porthole 34. This closure constitutes the fast-acting valve that shuts off the steady gas flow used in the permeability measurement. In the interval immediately after the termination of fluid flow, the transient signal from transducer 30 is recorded in the memory of the computer (not shown) for subsequent recall and processed into the porosity measurement.

Reference is now made to FIG. 5, depicting an alternative design of the fast acting valve to be incorporated into probe 2. In this alternative embodiment, the fast acting valve is operated electro-mechanically and is directly driven by a solenoid 72. This alternative embodiment utilizes the same form of transducer 30 as is employed in the preferred embodiment. Prior to assembly, however, the top end of transducer 30 is coaxially disposed within a polished non-magnetic metal tube 50 around which a ring 52 has been fastened. The annular space between transducer 30 and polished tube 50 is filled with a conductive epoxy resin 54. Brass body 56 includes an internal groove 57 in which is disposed O-ring 58 such that a gas tight seal is formed between brass body 56 and the exterior of polished tube 50, which nevertheless permits polished tube 50 to slide axially inside brass body 56

Air is supplied for the permeability measurement through drilled hole 60 in brass body 56. Return spring 62 biases the transducer 30 and polished tube 50 up against a stop formed by annular ridge 63 on the inside of brass solenoid spool 64. During this period, air is freely supplied through drilled hole 60 to the entire cavity 90 below the opening of rubber tip 66, which, in the preferred embodiment, is compressed against the sample 42 to form a seal preventing gas flow along the surface of 42. Brass body 56 may include an extension 71 that butts against the face of sample 42 when rubber tip 66 is sufficiently compressed, thereby preventing over compression of rubber tip 66. In order that the flow of gas out of sample 42 is not impeded or redirected thereby, the extension 71 of brass body 56 is pierced by a plurality of release holes 70,70'.

Subsequent to the acquisition of the permeability data, the porosity measurement phase is performed. The porosity determination is initiated by sending current to a solenoid 72, which forces soft iron armature 74 downwards. Since armature 74 is attached to the polished tube 50 and transducer 30, the latter two elements are likewise moved downwards. This action forces the shoulder 73 just above the diaphragm of transducer 30 to seal against the top 68 of rubber tip 66, isolating the small cavity 90 below transducer 30 and allowing pressure in cavity 90 to decline. The transient voltage signal from transducer 30 is conducted to the analog-to-digital converter (ADC) card in the computer (not shown) via wires 76 and 78, soldered to pin 81 at the upper end of transducer 30 and molded into the conductive epoxy 54 respectively. From the permeability measurement performed earlier, the computer computes the appropriate intervals at which pressure measurements are made using transducer 30. When the pressure has decayed sufficiently for the required measurements to have been made, the values of both the porosity and of the volume of cavity 90 may be computed.

The mode of calculating sample porosity may now be described. FIG. 6 and shows a family of nine pressure decay curves, for rock of different porosities ranging from 5% to 45%, in a situation where the cavity volume, the tip dimensions and the initial pressure are all held constant.

The symbol mD is the dimensionless pressure function:

$$mD = \frac{P^2 - P^2_{atm}}{P^2_{init} - P^2_{atm}}$$

and the symbol tD represents dimensionless time:

$$tD = \frac{kP_{init}t}{\mu d^2}$$

where k is the permeability, $\mu$ is the gas viscosity and d is the inner tip radius (all in consistent units). This set of curves has been calculated for the ratio of outer to inner tip radii, $b_D = 2.0$, and for the pressures $P_{init} = 1.25 \times 10^5$ Pascals, and $P_{atm} = 0.85 \times 10^5$ Pascals.

The changing curvature of the different curves are caused by the different porosities for which the curves were calculated, and enable calculation of the porosity of the rock. A simple means by which the curvature of the observed curve may be used to enable the calculation of porosity is by measurement of the dimensionless times that elapse before the pressure decay to two particular levels. The observation of the times at which the pressure has decayed to the two successive levels provides the data needed to ascertain the porosity from FIG. 7. In this figure there are again nine curves for the same different values of porosity. Crossing them are seven dashed lines for different cavity volumes. These cavity volumes are given in terms of a dimensionless cavity height $h_D$, which is defined as the cavity height divided by the inner tip radius. The axes of the graph, tD1 and tD2, are the values of dimensionless time by which the dimensionless pressure function has declined to 30% and to 5%, respectively, of the initial value of mD=1.

Stored in the computer's memory are parameters that describe several curves of the type depicted in FIG. 7. The particular curves in memory are those appropriate to two constant parameters: (1) the ratio of outer diameter D to inner diameter d of the tip of probe 2; and (2) the ratio of the steady gauge pressure used for the permeability measurement to the absolute value of the atmospheric pressure at the location where the readings are performed. The dimensionless times, measured at two different relative values of the pressure, serve as the input data; e.g. 0.3 and 0.05 were selected as tD1 and tD2 for the graph of FIG. 7. A program in the computer is used to find which of the set of curves (i.e. which porosity value) best describes the observation.

The ability of the system to separately and consecutively compute both porosity and cavity volume is attributable to the differing influences these two factors have on the shape of the pressure decay curve. If cavity volume is large-such that it dominates the decay—the logarithm of the pressure function decreases linearly with time. Conversely, if the cavity is small relative to the pore volume of the affected sample, such that most of the gas trapped after the fast-acting valve is closed is that in the pores of the sample, then the logarithm of the pressure function would decrease more rapidly at short times, and more slowly as the time increases. Because these two effects are distinguishable, independent values of porosity and cavity volume can be made.

Subsequently to a verification that the cavity volume value is within the expected range, the computed value of the porosity is accepted. Both the values for permeability and porosity may be immediately displayed in an LED or other readout, and also recorded to the computer memory for later use.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents and publications cited above are hereby incorporated by reference.

What is claimed is:

1. A single apparatus for consecutively determining both the permeability and the porosity of a sample of a substance, said apparatus comprising:

means for measuring the rate of a fluid flow through a surface of the sample;

means for measuring the pressure of a fluid above a surface of the sample;

means for quantifying elapsed times required for the pressure of the fluid above the surface of the sample to decrease to two pre-selected levels; and means for comparing the elapsed times required for the pressure to decrease to two pre-selected levels to corresponding values pertaining to a substance of known porosity.

2. A single apparatus for consecutively determining both the permeability and the porosity of a sample of a substance, said apparatus comprising:

means for supplying a fluid under a known constant pressure, thereby inducing a fluid flow;

probe means for directing the fluid flow through a surface of the sample;

means for measuring the rate of the fluid flow through a surface of the sample, comprising means for measuring elapsed time for flow through the surface of a known quantity of the fluid at the known constant pressure;

means for abruptly terminating the fluid flow and thereby temporarily trapping a quantity of the fluid in the pores of a portion of the sample below said directing probe means and within a cavity defined by said probe means and the surface;

means for measuring the pressure of the fluid trapped within said cavity;

means for quantifying elapsed times required for the pressure of the fluid within said cavity to decrease to two pre-selected levels; and means for comparing the elapsed times required for the pressure to decrease to two pre-selected levels to corresponding values pertaining to a substance of known porosity.

3. The apparatus of claim 2 wherein said means for supplying a fluid comprises a variable volume chamber.

4. The apparatus of claim 3 wherein said variable volume chamber comprises:

bellows means for containing said fluid;

means for maintaining a constant biasing force upon said bellows means, said force directed toward the interior of said bellows means;

means for controllably pumping said fluid into said bellows means;

means for controllably releasing said fluid from said bellows means; and means for transmitting said fluid flow to said probe means for directing said fluid flow.

5. The apparatus of claim 4 wherein said maintaining means comprises a mass of known weight.

6. The apparatus of claim 4 wherein said maintaining means comprises at least one constant-force spring.

7. The apparatus of claim 4 wherein said means for measuring elapsed time comprises means, adjacent to said bellows means, for measuring the contraction of said bellows means caused by the release of said fluid therefrom by said controllable release means.

8. The apparatus of claim 7 wherein said means for measuring contraction comprises photodetector means for detecting movement.

9. The apparatus of claim 8 wherein said photodetector means for detecting movement comprises:

a fixed frame disposed proximately to said bellows means;

at least one source of light disposed on said frame;

means for sensing light disposed on said frame; and film, comprising alternate opaque and transparent portions, disposed upon said bellows means and between said source of light and said sensing means.

10. The apparatus of claim 7 wherein said means for measuring contraction comprises interferometer means for detecting movement.

11. The apparatus of claim 10 wherein said interferometer means for detecting movement comprises:
   a fixed frame disposed proximately to said chamber means for containing;
   means, attached to said frame, for generating an electromagnetic energy beam;
   first means for reflecting electromagnetic energy, disposed upon said diaphragm means for holding said fluid;
   second means for partially reflecting electromagnetic energy, attached to said frame parallel to said first reflecting means; and
   means for detecting the intensity of said electromagnetic energy beam.

12. The apparatus of claim 11 wherein said generating means comprises a laser.

13. The apparatus of claim 3 wherein said variable volume chamber comprises:
   rigid, open chamber means for containing said fluid;
   flexible diaphragm means for holding said fluid within said containing means, said holding means disposed across the opening in said chamber;
   means for maintaining a constant biasing force upon said diaphragm holding means, said force directed toward the interior of said containing means;
   means for controllably pumping said fluid into said containing means; and
   means for controllably releasing said fluid from said containing means.

14. The apparatus of claim 13 wherein said maintaining means comprises a mass of known weight.

15. The apparatus of claim 13 wherein said maintaining means comprises at least one constant-force spring.

16. The apparatus of claim 13 wherein said means for measuring elapsed time comprises means, adjacent to said diaphragm means for holding said fluid, for monitoring the displacement of said diaphragm means caused by the release of said fluid from said containing means by said controllable release means.

17. The apparatus of claim 16 wherein said means for monitoring displacement comprises interferometer means for detecting movement.

18. The apparatus of claim 17 wherein said interferometer means for detecting movement comprises:
   a fixed frame disposed proximately to said chamber means for containing;
   means, attached to said frame, for generating an electromagnetic energy beam;
   first means for reflecting electromagnetic energy, disposed upon said diaphragm means for holding said fluid;
   second means for partially reflecting electromagnetic energy, attached to said frame parallel to said first reflecting means; and
   means for detecting the intensity of said electromagnetic energy beam.

19. The apparatus of claim 18 wherein said generating means comprises a laser.

20. The apparatus of claim 16 wherein said means for monitoring displacement comprises photodetector means for detecting movement.

21. The apparatus of claim 20 wherein said photodetector means for detecting movement comprises:
   a fixed frame disposed proximately to said bellows means;
   at least one source of light disposed on said frame;
   means for sensing light disposed on said frame; and
   film, comprising alternate opaque and transparent portions, disposed upon said bellows means and between said source of light and said sensing means.

22. The apparatus of claim 2 wherein said means for abruptly terminating said fluid flow comprises:
   a rigid body disposed in said probe means;
   an outer wall disposed around said body;
   pressure transducer means for measuring pressure changes, said transducer means disposed within said body;
   flexible molding means for arresting said fluid flow, said arresting means disposed about said transducer means for measuring;
   means for channeling said fluid flow between said transducer measuring means and said arresting means to the surface; and
   means for controllably forcing fluid between said arresting means and said outer wall, thereby abruptly biasing said arresting means against said measuring means and terminating said fluid flow between said measuring means and said arresting means.

23. The apparatus of claim 2 wherein said means for abruptly terminating said fluid flow comprises:
   a rigid body disposed in said probe means;
   pressure transducer means for measuring pressure changes, said transducer means slidably disposed within said body;
   means for biasing said transducer measuring means upward within said body;
   flexible molding means for arresting said fluid flow;
   means for channeling said fluid flow through said body, between said transducer measuring means and said molding means, to the surface; and
   solenoid means for controllably sliding said transducer means for measuring into contact with said flexible annular tip, thereby abruptly terminating said fluid flow between said transducer measuring means and molding means.

24. The apparatus of claim 2 wherein said means for measuring pressure change comprises a piezoelectric transducer disposed within said probe means.

25. A method for consecutively determining both the permeability and the porosity of a sample of a substance, the method comprising the steps of:
   (a) supplying a fluid under a known constant pressure, thereby inducing a fluid flow;
   (b) measuring the elapsed time for the flow through a surface of the sample of a known quantity of the fluid at the known constant pressure;
   (c) measuring the pressure of a fluid above a surface of the sample;
   (d) quantifying elapsed times required for the pressure of the fluid above the surface of the sample to decrease to two pre-selected levels; and
   (e) comparing the elapsed times required for the pressure to decrease to two pre-selected levels to corresponding values pertaining to a substance of known porosity.

26. The method of claim 25 wherein the step of supplying a fluid comprises utilizing a variable volume chamber.

27. The method of claim 26 wherein the step of utilizing a variable volume chamber comprises the steps of:
(a) containing the fluid in a bellows;
(b) controllably pumping the fluid into the bellows;
(c) controllably releasing the fluid from the bellows; and
(d) transmitting the fluid flow to the probe.

28. The method of claim 27 wherein the step of measuring elapsed time comprises measuring the contraction of the bellows caused by the controllable release of the fluid therefrom.

29. The method of claim 28 wherein the step of measuring contraction comprises employing a photodetector to detect movement.

30. The method of claim 29 wherein the step of employing a photodetector comprises the steps of:
(a) providing a fixed frame proximately to the bellows;
(b) placing at least one source of light on the frame;
(c) attaching a photosensor on the frame; and
(d) disposing a film, comprising alternate opaque and transparent portions, upon the bellows between the source of light and the photosensor.

31. The method of claim 26 wherein the step of utilizing a variable volume chamber comprises the steps of:
(a) providing a rigid, open chamber;
(b) disposing a flexible diaphragm across the opening in the chamber, thereby holding the fluid within the chamber;
(c) maintaining a constant biasing force upon the diaphragm, the force directed toward the interior of the chamber;
(d) controllably pumping the fluid into the chamber; and
(e) controllably releasing the fluid from the chamber.

32. The method of claim 31 wherein the step of maintaining comprises placing a mass of known weight on the diaphragm.

33. The method of claim 31 wherein the step of maintaining comprises disposing at least one constant-force spring.

34. The method of claim 31 wherein the step of measuring elapsed time comprises means monitoring the displacement of the diaphragm caused by the release of the fluid from the chamber.

35. The method of claim 34 wherein the step of monitoring displacement comprises engaging an interferometer to detect movement.

36. The method of claim 35 wherein the step of engaging an interferometer comprises the steps of:
(a) disposing a fixed frame proximately to the chamber;
(b) generating an electromagnetic energy beam;
(c) placing a first electromagnetic energy reflector upon the diaphragm;
(d) fixing, to the frame and parallel to the first reflector a semi-transparent electromagnetic energy second reflector;
(e) splitting the electromagnetic beam into two beams by passing a fraction of the beam through the semi-transparent second reflector;
(f) reflecting the two beams off both the reflectors and toward a single electromagnetic energy detector; and
(g) detecting fluctuations in the intensity of the two beams attributable to interference between the two beams.

37. The method of claim 36 wherein the step of generating comprises engaging a laser.

38. A method for consecutively determining both the permeability and the porosity of a sample of a substance, the method comprising the steps of:
(a) supplying a fluid under a known constant pressure thereby inducing a fluid flow;
(b) measuring the elapsed time for the flow through a surface of the sample of a known quantity of the fluid at the known constant pressure;
(c) directing the fluid flow through a probe then through the surface of the sample;
(d) abruptly terminating the fluid flow and thereby temporarily trapping a quantity of the fluid within a cavity defined by the directing probe and the surface;
(e) measuring the pressure of the fluid trapped within the cavity;
(f) quantifying elapsed times required for the pressure of the fluid trapped within the cavity to decrease to two pre-selected levels; and
(g) comparing the elapsed times required for the pressure to decrease to two pre-selected levels to corresponding values pertaining to a substance of known porosity.

39. The method of claim 38 wherein the step of abruptly terminating the fluid flow comprises the steps of:
(a) disposing a rigid body in the probe;
(b) placing an outer wall around the body;
(c) fixing a pressure transducer within the body;
(d) providing around the transducer a flexible molding;
(e) channeling the fluid flow between the transducer and the molding to the surface; and
(f) controllably forcing fluid between the molding and the outer wall, thereby biasing the molding against the transducer and terminating the fluid flow between the transducer and the molding.

40. The method of claim 38 wherein the step of abruptly terminating the fluid flow comprises the steps of:
(a) placing a rigid body in the probe;
(b) slidably disposing a pressure transducer within the body;
(c) biasing the transducer measuring means upward within the body;
(d) channeling the fluid flow through the body, between the transducer and the annular tip, to the surface; and
(e) activating a solenoid to controllably slide the transducer into contact with the annular tip, thereby terminating the fluid flow between the transducer and the flexible tip.

41. The method of claim 38 wherein the step of measuring pressure change comprises the step of disposing a piezoelectric transducer within the probe.

* * * * *